US006215303B1

(12) United States Patent
Weinstock et al.

(10) Patent No.: US 6,215,303 B1
(45) Date of Patent: Apr. 10, 2001

(54) WIRE DETECTION SYSTEM

(75) Inventors: Harold Weinstock, Springfield, VA (US); Nilesh Tralshawala, Greenbelt, MD (US)

(73) Assignee: The United States of America as represented by the Secretary of the Air Force, Washington, DC (US)

(*) Notice: Subject to any disclaimer, the term of this patent is extended or adjusted under 35 U.S.C. 154(b) by 0 days.

(21) Appl. No.: 09/332,639

(22) Filed: Jun. 14, 1999

(51) Int. Cl.[7] .................................................. G01R 33/00
(52) U.S. Cl. .......................... 324/263; 324/248; 505/846
(58) Field of Search .................................... 324/263, 248, 324/239, 240; 505/845, 846

(56) References Cited

U.S. PATENT DOCUMENTS 4,982,158 * 1/1991 Nakata et al. ........................ 324/263

* cited by examiner

Primary Examiner—Walter E. Snow
(74) Attorney, Agent, or Firm—William G. Auton

(57) ABSTRACT

A SQUID (Superconducting Quantum Interference Device) magnetometer, by far the most sensitive means for detecting small magnetic field variations, is utilized to detect defects inadvertently produced in the manufacture and draw-down of wires. Detection is effected by moving any electrically-conducting wire directly under a shielded SQUID magnetometer with a small aperture to permit the sensing of the magnetic field associated with injected or induced alternating electrical current. Shielding may be provided either by a mu-metal cylinder with a small concentric bottom hole or an open superconducting cylinder strategically placed around the SQUID sensor. Initially, the position of the cryogenic containment vessel (dewar) is oriented to produce a null magnetic signal at the squid sensor location. Any phase-sensitive-detected) signal that appears after wire is spooled under the sensor must be related to non-concentric deviations of the current path in the wire. These deviations can be caused by foreign inclusions, structural anomalies or an irregular geometrical cross section. This technique is especially effective in verifying the integrity of composite wires where it is not possible to visually inspect the embedded wire components, e.g., multifilament superconducting wire encased in a copper matrix. The region of non-uniform current can be localized immediately, and appropriate action can be taken whether to terminate the spooling process or to note the effect for future action.

1 Claim, 1 Drawing Sheet

WIRE DETECTION SYSTEM

STATEMENT OF GOVERNMENT INTEREST

The invention described herein may be manufactured and used by or for the Government for governmental purposes without the payment of any royalty thereon.

BACKGROUND OF THE INVENTION

The present invention relates generally to reliability, and more specifically this invention permits monitoring of the structural and geometrical integrity of electrically-conducting wires during the manufacturing process, or it may be utilized to inspect the integrity of wires at any time after manufacture. Unlike many other inspection techniques which assess only defects observable on the surface, this invention provides instantaneous information on defect structures within the interior of the wires, as well as on the surface. Given this unique diagnostic ability, it is possible to improve quality control and to avoid manufacturing down-time and waste. For wire already produced, this invention provides an inspection technique for verifying the integrity of the wire prior to its use in a given application. Although this invention pertains most simply to any conductor with a circular cross section, it applies equally well to any long length of conductor with arbitrary cross section and composition, regardless of whether the conductor is referred to as a wire, tape, cable or some other designation. For the case of wires with composite internal structure, this invention permits one to validate the uniformity of the internal structure and to detect deviant features.

The following patents are examples of prior art, the disclosures of which are incorporated herein by reference:

U.S. Pat. No. 5,729,135 Mar. 17, 1998 Kugai and Hyogo
U.S. Pat. No. 5,572,123 Nov. 5, 1996 Wikswo, Jr., et al.
U.S. Pat. No. 5,109,196 Apr. 28, 1992 Wikswo, Jr., et al.
U.S. Pat. No. 4,982,158 Jan. 1, 1991 Nakata et al.
U.S. Pat. No. 5,610,517 Mar. 11, 1997 Ma et al.

It is common in the manufacture of vast lengths of conducting wires to start with a large-diameter, relatively small-length volume of the conducting (generally metallic) material and to pull it through a succession of dyes, each time reducing the diameter and increasing the length of the material. This process can introduce strain in the wire and small geometrical asymmetries of defect structures dependent on the condition of the dye and the forces applied. Additionally, the initial bulk material may have contained a variety of impurity substances or small inclusive volumes of material whose physical properties differ significantly from that of their surroundings. As wire is drawn down to smaller and smaller diameters, their material anomalies can have a profound effect on the drawing process. For example, an inclusive impurity volume although small, becomes a relatively larger hazard as the diameter of the host material is decreased, possibly resulting in a high probability of wire rupture during the drawing process. When such an event occurs, the process must be discontinued and the ruptured wire removed before resuming the operation. The waste wire material and manufacturing down-time are costly consequences of the inability to monitor on-line the structural integrity of the wires being produced. Sometimes the rupture can result from surface irregularities. While there are various techniques capable of detecting surface irregularities on the wire, none of these is capable of reliably detecting internal defects. occasionally, the surface defects are responsible for wire rupture, bit in many instances, the vast majority of ruptures (e.g., over 80% for aluminum wire with 0.1% of embedded silicon inclusions) occur due to included impurities.

SUMMARY OF THE INVENTION

The key element of this invention is a superconducting (SQUID) magnetic field sensor which is used to detect small magnetic anomalies produced by alternating electrical current, provided by a constant-current power supply. The SQUID is shielded from undesirable environmental signals by a superconducting, open-ended cylindrical shield or by a cylindrical magnetically-shielded container with a suitably-sized hole in its bottom plate. Alternately, a SQUID gradiometer configuration may be used to cancel undesirable environmental magnetic signals. The signal generated by the magnet field produced by the current in the wire and detected by the SQUID is transmitted from the cryogenic region in the dewar by an electrical cable to flux-locked-loop circuitry located just outside the dewar. The rectified output signal from this circuitry is carried to one input of a lock-in amplifier, with the other input coming from the constant-current AC power supply. The output of the lock-in amplifier is correlated with information on the motion of the wire in a data storage unit and can be printed upon demand in the form of a graph of magnetic signal versus distance along the wire. The current passes through the wire under test, while the wire itself passes through a fairly tight-fitting guide at a given speed under the SQUID sensor. A drive motor may be used to power a take-up reel, and the wire either originates from a supply reel or as a result of being drawn through a die. Although, in principle, this form of defect detection can employ a direct electrical current, the invention is most sensitive when phase-sensitive detection via a lock-in amplifier is utilized in conjunction with a low-frequency alternating current. Typically, a frequency range of 100 to 2,000 Hz is used, although not at a frequency which is an integer multiple of the prevailing input line frequency, i.e., 60 Hz in the USA and 50 Hz in most other countries. The electrical current may be applied most simply by providing pressure contact points and along the wire on both sides of the wire.

It is an object to permit monitoring of the structural and geometrical integrity of electrically-conducting wires during the manufacturing process, or to inspect the integrity of wires at any time after manufacture.

These and many other objects and advantages of the present invention will be readily apparent to one skilled in the pertinent art from the following detailed description of a preferred embodiment of the invention and the related drawings.

DESCRIPTION OF THE DRAWINGS

The sole FIGURE of the drawings is FIG. 1 which is a block diagram of the invention.

DETAILED DESCRIPTION OF THE PREFERRED EMBODIMENT

Figure 1:
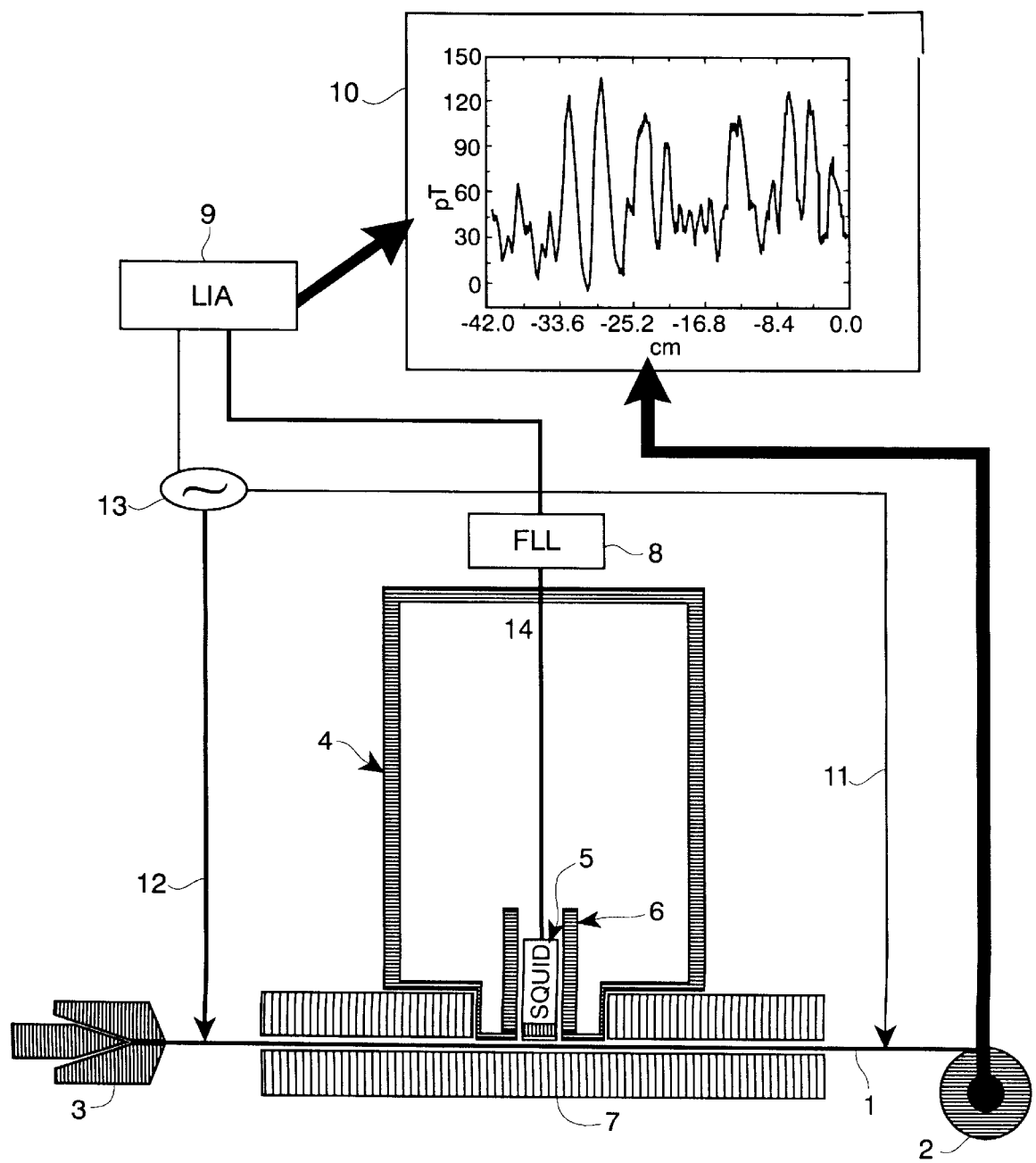

The schematic drawing of this invention is shown in FIG. 1. The key element of this invention is a superconducting (SQUID) magnetic field sensor (5) which is used to detect small magnetic anomalies produced by alternating electrical current, provided by a constant-current power supply (13). The SQUID is shielded from undesirable environmental signals by a superconducting, open-ended cylindrical shield or by a cylindrical magnetically-shielded container with a suitably-sized hole in its bottom plate. Alternately, a SQUID gradiometer configuration may be used to cancel undesirable environmental magnetic signals. The signal generated by the magnet field produced by the current in the wire (1) and detected by the SQUID is transmitted from the cryogenic region in the dewar (4) by an electrical cable (14) to the flux-locked-loop circuitry (8) located just outside the dewar. The rectified output signal from this circuitry is carried to one input of the lock-in amplifier (9), with the other input coming from the constant-current AC power supply for the display (10), which measures and displays the LIA signal. The output of the lock-in amplifier is correlated with information on the motion of the wire in a data storage unit and can be printed upon demand in the form of a graph of magnetic signal versus distance along the wire. The current passes through the wire under test, while the wire itself passes through a fairly tight-fitting guide (7) at a given speed under the SQUID sensor. A drive motor (2) may be used to power a take-up reel, and the wire either originates from a supply reel (3) or as a result of being drawn through a die. Although, in principle, this form of defect detection can employ a direct electrical current, the invention is most sensitive when phase-sensitive detection via a lock-in amplifier is utilized in conjunction with a low-frequency alternating current. Typically, a frequency range of 100 to 2,000 Hz is used, although not at a frequency which is an integer multiple of the prevailing input line frequency, i.e., 60 Hz in the USA and 50 Hz in most other countries. The electrical current may be applied most simply by providing pressure contact points (11 and 12) and along the wire on both sides of and at some distance from the SQUID sensing element and its containing dewar. However, current also can be introduced inductively, that is, by introducing an eddy current in the wire created by a primary source of alternating current nearby, either within the SQUID dewar or external to it.

Minimizing the separation distance between the SQUID sensor and the wire being inspected maximizes sensitivity of this detection method. Also, extraneous noise is reduced by channeling the wire through a groove in the wire guide which is just wide enough to allow the wire to move easily with little friction against the walls of the groove. This keeps the wire straight and directly under the SQUID sensor. The depth of the groove also is matched to the diameter of the wire so that the stand-off separation is minimized. The groove, several inches in length may be machined into any convenient non-electrically-conducting material.

This non-destructive method of evaluating the integrity of both simple and composite wires is easily adaptable in a variety of environments, including that in which the wires are being manufactured. When unwanted anomalies are sensed, a signal can be emitted which can terminate the drawing process. This will eliminate wire breakage and permit the practical use of the drawn wire without subjecting it to additional drawing that would end in wasted time and material. This method also can be applied to testing wires that have been in storage and which may have deteriorated over some period of time.

This method for wire inspection is less complicated and differs from that disclosed in U.S. Pat. No. 5,729,135, the disclosure of which is incorporated herein by reference. In that method, the entire cryogenic system, which also uses a SQUID magnetic sensor in a dewar, must be enclosed within a magnetically-shielded container. This container must also hold a magnet which generates a uniform magnetic field in the vicinity of the wire. Anomalies in the wire are detected by distortions of the applied magnetic field. Thus, this method employs an external applied magnetic field and depends on a variation in magnetic susceptibility of the wire to detect wire anomalies. The present disclosure depends on variations in the path of applied electrical current to detect wire anomalies by observing the distortion of the magnetic field produced by the flow of electrical current. It is a more direct approach than that of the earlier patent and is not dependent on the delicate balancing of the applied magnetic field signal to keep it from saturating the SQUID sensor. It requires less space, has fewer components and requires less electrical power.

The other 4 U.S. Patents cited all involve the use of SQUID detection of structural anomalies in a variety of structures, but none that remotely resembles a simple or composite wire. For the most part, rather complex analyses are required to detect structural defects producing magnetic field anomalies. To a major extent the foundation of those patents is the earlier research (cited in the list of prior publication) of one of the current inventors (HW). In that study, current was passed through a length of pipe about 2" in diameter, and the pipe was moved under the SQUID, and at some distance from it, by hand. Rather large holes in the pipe were detectable in the form of magnetic field anomalies.

Many different forms of gradiometer configurations, both planar and axial, may be used in place of the superconducting or magnetic shield, or they may be used in conjunction with such shields to provide better signal resolution. Gradiometer coils are arranged so that they cancel uniform background magnetic fields, or in the case of higher-order gradiometers, they can cancel background fields that vary as a function of distance. These gradiometer coils then pick up a signal that is sensed by an otherwise shielded SQUID sensor. Another key to better signal resolution relates to placing the gradiometer coils or the SQUID magnetometer sensor as close as possible to the wire being tested. This can be effected by placing the sensor or the coils in a vacuum space just a minute distance from a very thin bottom plate of the dewar vessel. Under some circumstances it also may be possible to replace the method in which a cryogenic fluid is used, typically either liquid nitrogen or liquid helium, by a mechanical refrigeration unit. However, care must be exercised in keeping unwanted electromagnetic noise and vibrations generated by such a unit from degrading the signal-to-noise ratio of the SQUID sensor.

A potential variation of this invention is the use of a moving SQUID sensing unit over wires and cables which are stationary. This is an application for which either current normally passes through these wires and cables, or current may be injected so that the structural integrity of these entities may be evaluated.

While the invention has been described in its presently preferred embodiment, it is understood that the words which have been used are words of description rather than words of limitation and that changes within the purview of the appended claims may be made without departing from the scope and spirit of the invention in its broader aspects.

What is claimed is:

1. A system for detecting a defect in a wire comprising:
   a means for sending an alternating current signal into the wire and which generates a magnetic field thereby wherein said wire is fed from a supply reel, through a wire guide to a take-up reel, and wherein said sending means comprises: a power source which produces the current signal; and a set of pressure contact points which conduct the current signal from the power source to said wires as it flows through the wire guide;
   a means for displaying an output signal; a superconducting magnetic field sensor that produces an output signal when sensing the magnetic field around the wire, said output signal having recognizable characteristics of magnetic anomalies when defects are present in the wire wherein said superconducting magnetic field sensor is enclosed in a dewar which provides an electrical connection between the superconducting magnetic field sensor and a lock-in amplifier which amplifies the output signal of the superconducting magnetic field sensor for the displaying means; and a superconducting open-ended cylindrical shield that shields the superconducting magnetic field sensor from any undesirable environmental signals that could contaminate readings.

* * * * *

UNITED STATES PATENT AND TRADEMARK OFFICE
Certificate

Patent No. 6,215,303 B1                                                                                           Patented: April 10, 2001

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Harold Weinstock. Springfield, VA; Nilesh Tralshawala, Greenbelt. MD; and James Ronald Claycomb, Houston, TX.

Signed and Sealed this Sixteenth Day of July 2002.

*EDWARD LEFKOWITZ*
*Supervisory Patent Examiner*
Art Unit 2862